United States Patent
Okaniwa et al.

(10) Patent No.: US 10,888,214 B2
(45) Date of Patent: Jan. 12, 2021

(54) ENDOSCOPE SYSTEM INCLUDING OVERTUBE AND ENDOSCOPE HAVING RIGIDITY CHANGING MECHANISM

(71) Applicant: OLYMPUS CORPORATION, Tokyo (JP)

(72) Inventors: Suguru Okaniwa, Hachioji (JP); Seisuke Takase, Hachioji (JP); Hidehiro Joko, Hachioji (JP); Isamu Nakajima, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 442 days.

(21) Appl. No.: 15/983,201

(22) Filed: May 18, 2018

(65) Prior Publication Data
US 2018/0263469 A1    Sep. 20, 2018

Related U.S. Application Data

(63) Continuation of application No. PCT/JP2016/083818, filed on Nov. 15, 2016.

(30) Foreign Application Priority Data

Nov. 20, 2015  (JP) .................................. 2015-227903

(51) Int. Cl.
*A61B 1/005* (2006.01)
*A61B 1/31* (2006.01)
(Continued)

(52) U.S. Cl.
CPC ........ *A61B 1/00078* (2013.01); *A61B 1/0052* (2013.01); *A61B 1/00082* (2013.01);
(Continued)

(58) Field of Classification Search
CPC ............ A61B 1/00078; A61B 1/00082; A61B 1/00135; A61B 1/00154; A61B 1/31; A61M 25/0054
See application file for complete search history.

(56) References Cited

U.S. PATENT DOCUMENTS

| 5,993,379 A | 11/1999 | Ouchi et al. |
| 6,293,908 B1 | 9/2001 | Fujikura et al. |

(Continued)

FOREIGN PATENT DOCUMENTS

| EP | 0827712 A2 | 3/1998 | |
| JP | 07213481 A * | 8/1995 | ......... A61B 1/00078 |

(Continued)

OTHER PUBLICATIONS

International Search Report dated Dec. 20, 2016 issued in PCT/JP2016/083818.

*Primary Examiner* — John P Leubecker
(74) *Attorney, Agent, or Firm* — Scully, Scott, Murphy & Presser, P.C.

(57) ABSTRACT

An endoscope system includes an endoscope including an insertion section formed in an elongated shape, a flexible tube portion provided at a proximal end side of the insertion section, and a rigidity changing mechanism portion provided inside the flexible tube portion, and configured to change rigidity of the flexible tube portion by an operation performed on a hand side, and a flexible overtube formed in a cylindrical shape extending in an axial direction, into which the insertion section is inserted, where a rigidity change region of the flexible tube portion by the rigidity changing mechanism portion is set to be from an intermediate portion to a proximal end portion of the flexible tube portion, and a total length of the overtube in the axial direction is set to be shorter than a total length of the rigidity change region.

2 Claims, 9 Drawing Sheets

(51) Int. Cl.
*A61B 1/00* (2006.01)
*A61M 25/00* (2006.01)
*G02B 23/24* (2006.01)
*A61M 25/06* (2006.01)
*A61B 1/05* (2006.01)
*A61B 1/06* (2006.01)

(52) U.S. Cl.
CPC ...... *A61B 1/00135* (2013.01); *A61B 1/00154* (2013.01); *A61B 1/00195* (2013.01); *A61B 1/05* (2013.01); *A61B 1/0676* (2013.01); *A61B 1/31* (2013.01); *A61M 25/0054* (2013.01); *A61M 25/0662* (2013.01); *G02B 23/24* (2013.01); *A61M 2025/0059* (2013.01)

(56) References Cited

U.S. PATENT DOCUMENTS

| | | | |
|---|---|---|---|
| 2001/0056220 | A1 | 12/2001 | Fujikura et al. |
| 2003/0233025 | A1* | 12/2003 | Saadat ............... A61B 1/0008 600/114 |
| 2007/0106118 | A1* | 5/2007 | Moriyama ......... A61B 1/00154 600/128 |
| 2012/0071722 | A1* | 3/2012 | Nakamura ......... A61B 1/00078 600/140 |
| 2016/0227982 | A1* | 8/2016 | Takahashi .......... A61B 1/00078 |
| 2016/0353980 | A1* | 12/2016 | Takahashi .......... A61B 1/00135 |
| 2020/0170489 | A1* | 6/2020 | Takahashi .......... A61B 1/0055 |

FOREIGN PATENT DOCUMENTS

| | | |
|---|---|---|
| JP | H10-234650 A | 9/1998 |
| JP | H10-276965 A | 10/1998 |
| JP | 2000-237124 A | 9/2000 |
| JP | 2000-237125 A | 9/2000 |
| JP | 2005-334474 A | 12/2005 |

* cited by examiner

ENDOSCOPE SYSTEM INCLUDING OVERTUBE AND ENDOSCOPE HAVING RIGIDITY CHANGING MECHANISM

CROSS REFERENCE TO RELATED APPLICATION

This application is a continuation application of PCT/JP2016/083818 filed on Nov. 15, 2016 and claims benefit of Japanese Application No. 2015-227903 filed in Japan on Nov. 20, 2015, the entire contents of which are incorporated herein by this reference.

BACKGROUND OF THE INVENTION

Field of the Invention

The present invention relates to an endoscope system provided with an endoscope including a rigidity changing mechanism portion in an insertion section, and an overtube.

Description of the Related Art

An endoscope including an image pickup unit, for picking up an optical image, inside a distal end portion of an insertion section that can be inserted from outside into inside a living body or inside a structure is used in medical and industrial fields, for example, to enable observation of a part where observation is difficult, such as inside a living body or inside a structure.

An endoscope disclosed in Japanese Patent Application Laid-Open Publication No. 10-276965 includes a rigidity changing mechanism portion configured to change rigidity of a part of an insertion section in a bending direction. The rigidity changing mechanism portion includes a coil pipe inserted through the insertion section, a wire inserted through the coil pipe, and a pulling mechanism portion configured to apply a compressive force to the coil pipe by pulling the wire. Rigidity of the coil pipe in the bending direction is changed according to an applied compressive force. Accordingly, rigidity of a part of the insertion section where the coil pipe is inserted is changed according to the compressive force applied to the coil pipe.

Furthermore, Japanese Patent Application Laid-Open Publication No. 2005-334474 discloses an endoscope system including an overtube which covers an insertion section to aid an insertion operation of an endoscope into a subject.

SUMMARY OF THE INVENTION

An endoscope system according to an aspect of the present invention includes an endoscope including an insertion section formed in an elongated shape, a flexible tube portion provided at a proximal end side of the insertion section, and a rigidity changing mechanism portion provided inside the flexible tube portion, and configured to change rigidity of the flexible tube portion, where a rigidity change region of the flexible tube portion by the rigidity changing mechanism portion is set to be from an intermediate portion to a proximal end portion of the flexible tube portion, and a flexible overtube formed in a cylindrical shape extending in an axial direction, into which the insertion section is slidably inserted, where the overtube is formed to have a total length in the axial direction that is shorter than a total length of the rigidity change region, and a degree of increase in rigidity in a state of covering the insertion section is set to be substantially equal to a degree of increase in the rigidity of the flexible tube portion caused by operation of the rigidity changing mechanism portion, where, by allowing, by changing relative positions of the overtube and the insertion section in a longitudinal direction in a state where the insertion section is covered by the overtube, selection between a state where a proximal end portion of the overtube in the axial direction is positioned on a most proximal end side of the insertion section and a distal end portion of the rigidity change region is exposed and a state where the overtube is displaced to a distal end side and the distal end portion of the rigidity change region is covered by the overtube, and by setting a degree of increase in rigidity, at a part of the insertion section where the overtube is covered, caused by the overtube covering the insertion section to be substantially equal, in a state where the insertion section is covered by the overtube, to the degree of increase in the rigidity of the flexible tube portion caused by operation of the rigidity changing mechanism portion, rigidity of a part of the insertion section which is on a distal end side with respect to the rigidity change region, a part of the rigidity change region exposed from the overtube, and a part covered by the overtube is gradually increased stepwise from a distal end of the insertion section in a proximal end direction, when an increase operation of rigidity of the rigidity change region is performed by the rigidity changing mechanism portion while the state where the proximal end portion of the overtube in the axial direction is positioned on the most proximal end side of the insertion section and the distal end portion of the rigidity change region is exposed is selected.

DETAILED DESCRIPTION OF THE PREFERRED EMBODIMENT(S)

Figure 1:
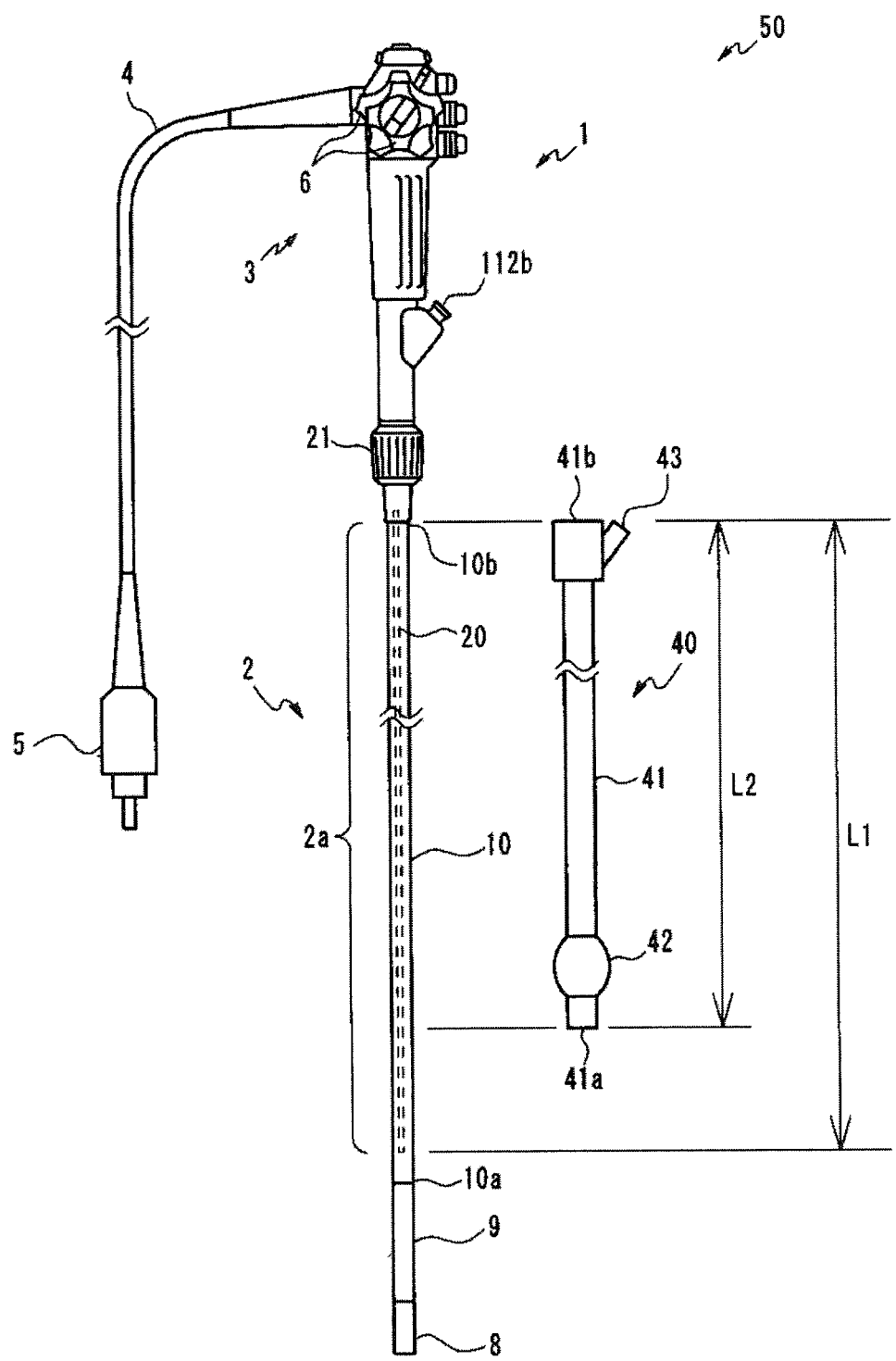
FIG. 1 is a diagram describing a configuration of an endoscope system.

Hereinafter, a preferred mode of the present invention will be described with reference to the drawings. Note that, in each of the drawings used in the following description, the scale of display may be different for each structural component such that each structural component is large enough to be recognized in the drawing, and the present invention is not limited to the modes shown in the drawings with respect to the number of structural components, the shapes of the structural components, the proportion of the sizes of the structural components, and the relative positional relationship of respective structural components.

An endoscope system 50 of the present embodiment shown in FIG. 1 includes an endoscope 1 and an overtube 40. The endoscope 1 includes an elongated insertion section 2 which can be introduced into a subject such as a human body, and the insertion section 2 has a configuration for observation of an inside of the subject. Note that the subject into which the insertion section 2 of the endoscope 1 is introduced is not limited to a human body, but may be another living body.

The endoscope 1 of the present embodiment is mainly configured of the insertion section 2 which is formed in an elongated shape to be introduced into a subject, an operation section 3 positioned at a proximal end of the insertion section 2, and a universal cord 4 extending from the operation section 3.

The insertion section 2 is configured of a distal end portion 8 installed at a distal end, a bendable bending portion 9 installed on a proximal end side of the distal end portion 8, and a flexible tube portion 10 having flexibility and connecting a proximal end side of the bending portion 9 and a distal end side of the operation section 3, where the distal end portion 8, the bending portion 9, and the flexible tube portion 10 are provided in a linked manner.

A configuration and the like for observing an inside of a subject are installed in the distal end portion 8. For example, an image pickup unit including an objective lens and an image pickup device and configured to optically observe the inside of the subject is installed in the distal end portion 8. Furthermore, although not shown, the distal end portion 8 is provided with an illumination light emitting unit configured to emit light configured to illuminate an object of the image pickup unit. Note that an ultrasound transducer for acoustically observing the inside of the subject by using ultrasound may be installed in the distal end portion 8.

The operation section 3 installed at the proximal end of the insertion section 2 is provided with an angle operation knob 6 for bending the bending portion 9. An endoscope connector 5 configured to be connectable to an external device, not shown, is provided at a proximal end portion of the universal cord 4. The external device to which the endoscope connector 5 is connected includes a camera control unit, and the like, configured to control the image pickup unit provided at the distal end portion 8.

Furthermore, the operation section 3 is provided with a rigidity changing knob 21 for operating a rigidity changing mechanism portion 20 installed inside the flexible tube portion 10. The rigidity changing mechanism portion 20 is inserted in the flexible tube portion 10 along a longitudinal direction of the flexible tube portion 10, and is configured such that rigidity to flexion is changed according to an operation input by the rigidity changing knob 21. That is, the rigidity changing mechanism portion 20 changes rigidity of the flexible tube portion 10 to flexion.

Figure 3:
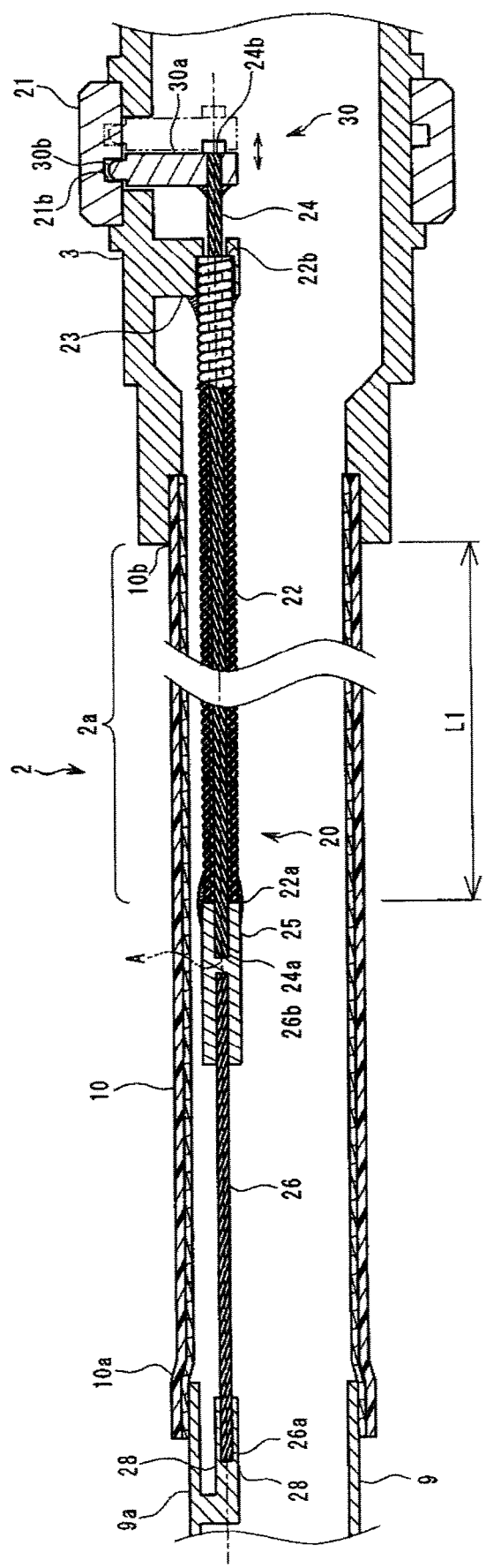
FIG. 3 is a diagram describing configurations of a flexible tube portion and a rigidity changing mechanism portion.

A configuration of the rigidity changing mechanism portion 20 is well known, and detailed description is omitted, but as shown in FIG. 3, the rigidity changing mechanism portion 20 includes a coil pipe 22, a first wire 24, a second wire 26, and a pulling mechanism portion 30. With respect to members configuring the insertion section 2 and the rigidity changing mechanism portion 20, a direction toward the distal end portion 8 side of the insertion section 2 will be referred to as a distal end direction, and a direction toward the operation section 3 side will be referred to as a proximal end direction.

The coil pipe 22 is a linear member formed by helically winding a linear wire of metal, such as stainless alloy, around a predetermined axis A parallel to the longitudinal direction of the insertion section 2, for example. A proximal end 22b of the coil pipe 22 is fixed to a coil fixing portion 23 provided inside the operation section 3.

Furthermore, a distal end 22a of the coil pipe 22 is disposed, in the flexible tube portion 10, in the proximal end direction by a predetermined distance with respect to a distal end 10a of the flexible tube portion 10. That is, the coil pipe 22 extends, inside the flexible tube portion 10, from the proximal end 10b of the flexible tube portion 10 and short of the distal end 10a of the flexible tube portion 10.

The first wire 24 is inserted through the coil pipe 22. A distal end 24a of the first wire 24 is fixed to the distal end 22a of the coil pipe 22, and a proximal end 24b of the first wire 24 is fixed to a wire holding portion 30a of the pulling mechanism portion 30 described later.

For example, in the present embodiment, the distal end 24a of the first wire 24 is fixed to a connecting portion 25 fixedly installed at the distal end 22a of the coil pipe 22. Note that the distal end 24a of the first wire 24 may be directly fixed to the distal end 22a of the coil pipe 22.

A distal end 26a of the second wire 26 is fixed to a wire fixing portion 28 provided at a frame member 9a on a proximal end side of the bending portion 9, and a proximal end 26b of the second wire 26 is fixed to the connecting portion 25. The second wire 26 restricts the distal end 22a of the coil pipe 22 from moving in the proximal end direction inside the flexible tube portion 10, and maintains a position of the coil pipe 22 in the longitudinal direction in the flexible tube portion 10.

The pulling mechanism portion 30 includes the rigidity changing knob 21 which rotates relative to the operation section 3, and the wire holding portion 30a which holds the proximal end 24b of the first wire 24 and which moves forward/backward in a direction along the axis A according to rotation of the rigidity changing knob 21.

A cam groove 21b is cut on an inner circumferential surface of the rigidity changing knob 21. The wire holding portion 30a is provided with a cam pin 30b which slidably engages with the cam groove 21b. Due to the engagement between the cam groove 21b and the cam pin 30b, the wire holding portion 30a moves forward/backward in the direction along the axis A according to rotation of the rigidity changing knob 21. The pulling mechanism portion 30 of the present embodiment configured in the above manner is capable of pulling the first wire 24 in the proximal end direction and changing tension applied to the first wire 24, according to a rotation operation of the rigidity changing knob 21 by a user.

A compressive force is applied to the coil pipe 22 according to the tension applied by the pulling mechanism portion 30 to the first wire 24. Resistance force of the coil pipe 22 to bending deformation is increased by application of the compressive force. Accordingly, rigidity of the flexible tube portion 10 to flexion, in a range where the coil pipe 22 is disposed inside, is changed according to the resistance force of the coil pipe 22 to bending deformation. With the configuration described above, the rigidity changing mechanism portion 20 changes the rigidity at a part, of the flexible tube portion 10, where the coil pipe 22 is inserted.

In the present embodiment, a length from the proximal end 10b of the flexible tube portion 10 to the distal end 22a of the coil pipe 22 in a state where the flexible tube portion 10 is linearly held is L1. Accordingly, a range, of the insertion section 2 of the endoscope 1 of the present embodiment, over the length L1 from the proximal end 10b of the flexible tube portion 10 in the distal end direction along the longitudinal direction is a rigidity change region 2a where rigidity can be changed by the rigidity changing mechanism portion 20.

Figure 2:
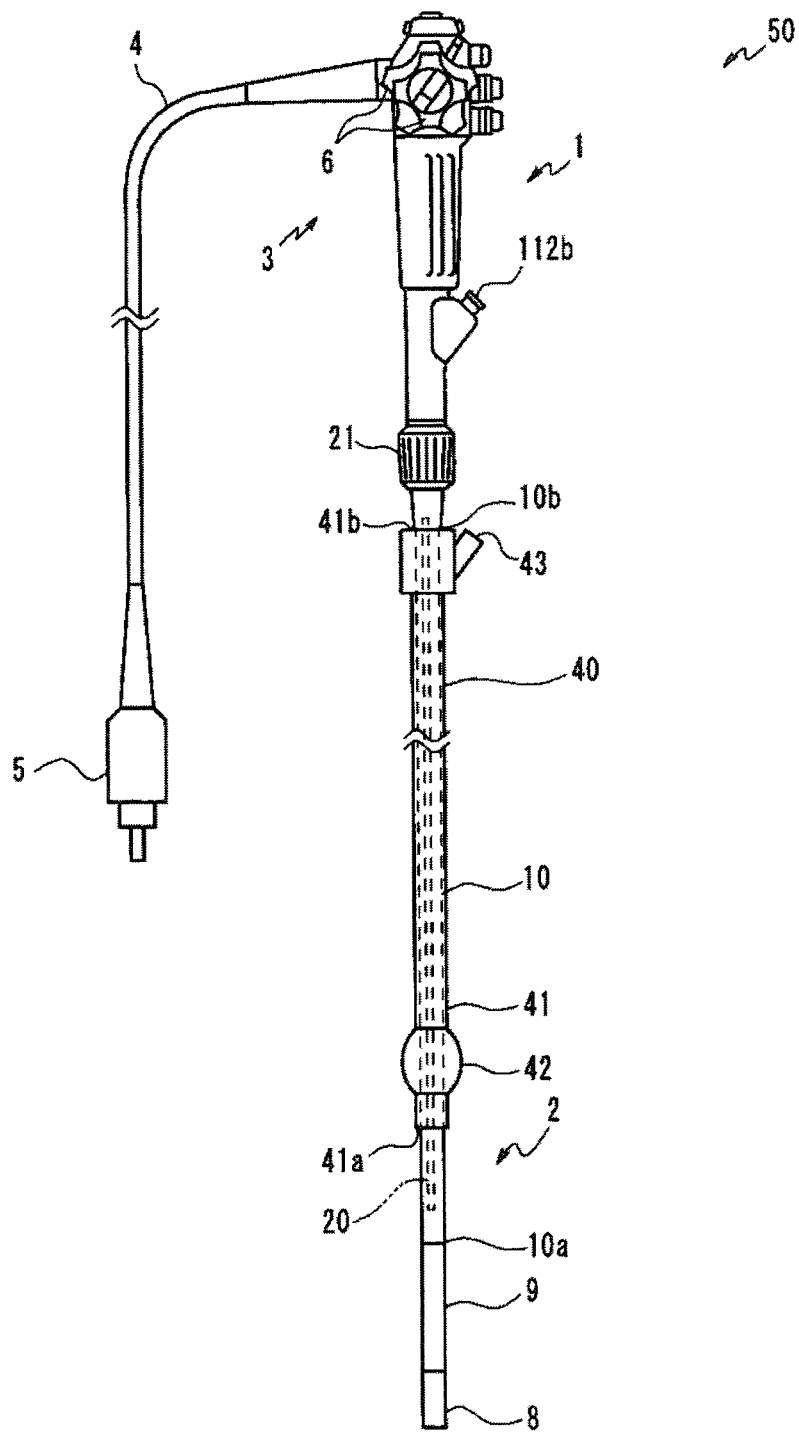
FIG. 2 is a diagram showing a state where an insertion section of an endoscope is covered by an overtube.

The overtube 40 includes a flexible cylindrical portion 41 having a cylindrical shape. The cylindrical portion 41 has a cylindrical shape which is open on both ends, and as shown in FIG. 2, allows insertion of the insertion section 2 of the endoscope 1. In other words, the cylindrical portion 41 may cover an outer circumference of the insertion section 2. In a state where the insertion section 2 is inserted inside, the cylindrical portion 41 flexes according to deformation of the insertion section 2. Furthermore, the cylindrical portion 41 is capable of sliding relative to the insertion section 2, along the longitudinal direction of the insertion section 2.

FIG. 2 shows a state where the cylindrical portion 41 is disposed in a most proximal end direction of the insertion section 2. That is, FIG. 2 shows a state where the insertion section 2 of the endoscope 1 is pushed deepest into the overtube 40.

As shown in FIGS. 1 and 2, a length L2 of the cylindrical portion 41 in an axial direction (longitudinal direction) is shorter than the length L1 of the rigidity change region 2a.

Accordingly, as shown in FIG. 2, in the case where the cylindrical portion 41 is disposed in the most proximal end direction of the insertion section 2, a distal end portion of the rigidity change region 2a provided at the flexible tube portion 10 protrudes in the distal end direction from a distal end portion 41a of the cylindrical portion 41 of the overtube 40. In other words, in the case where the insertion section 2 is pushed deepest into the cylindrical portion 41 of the overtube 40, the distal end portion of the rigidity change region 2a is exposed from the cylindrical portion 41 in the distal end direction.

A balloon 42, which is an expandable member, is installed at the distal end portion 41a of the cylindrical portion 41. Furthermore, a balloon air port 43 communicating with an inside of the balloon 42 via a pipe, not shown, is installed at a proximal end portion 41b of the cylindrical portion 41. The balloon 42 has a doughnut shape which is disposed to surround an outer circumference of the distal end portion 41a of the cylindrical portion 41. The balloon 42 expands or contracts according to inflow or outflow of air through the balloon air port 43.

As described above, with the endoscope system 50 of the present embodiment, the total length L2 of the cylindrical portion 41 of the overtube 40 covering the insertion section 2 is shorter than the length L1 of the rigidity change region 2a of the insertion section 2. Accordingly, with the endoscope system 50 of the present embodiment, by changing relative positions of the overtube 40 and the insertion section 2 in the longitudinal direction in a state where the insertion section 2 is covered by the overtube 40, selection between a state where the distal end portion of the rigidity change region 2a is exposed from the overtube 40 in the distal end direction and a state where the distal end portion of the rigidity change region 2a is covered by the overtube 40 is enabled.

Figure 4:
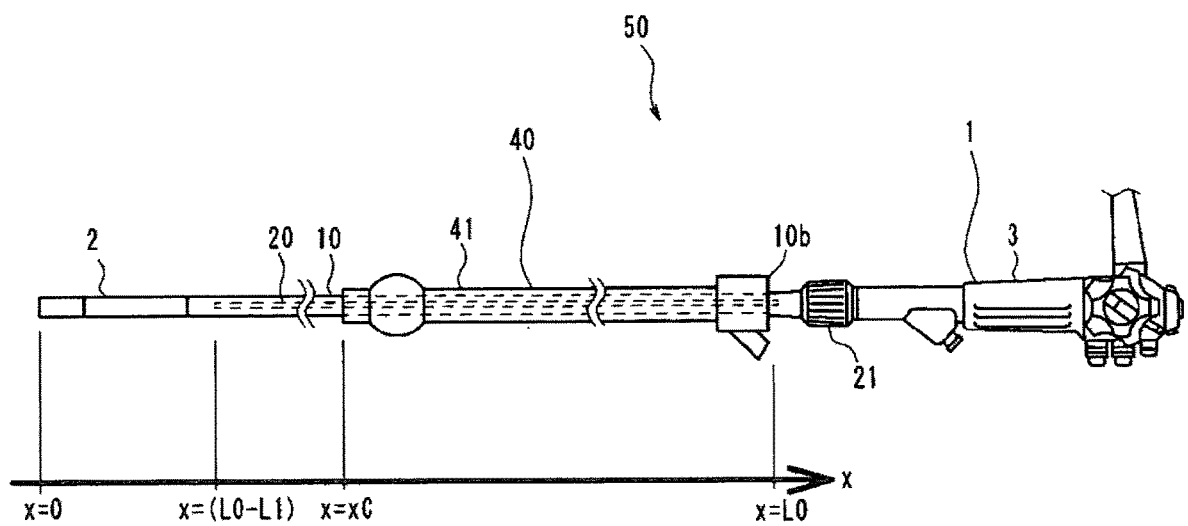
FIG. 4 is a diagram describing a positional relationship between the rigidity changing mechanism portion and the overtube.
Figure 5:
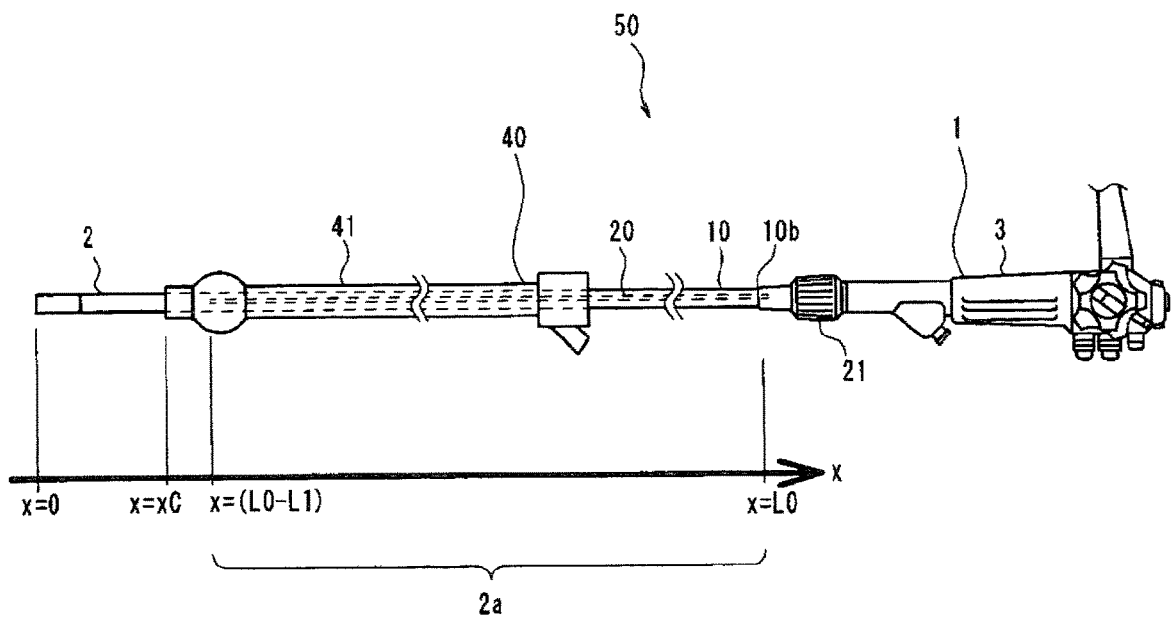
FIG. 5 is a diagram describing a positional relationship between the rigidity changing mechanism portion and the overtube.

For example, as shown in FIG. 4, when the insertion section 2 is relatively pushed in the distal end direction with respect to the overtube 40, the distal end portion of the rigidity change region 2a is exposed from the overtube 40 in the distal end direction. Moreover, for example, as shown in FIG. 5, when the insertion section 2 is relatively pulled back in the proximal end direction with respect to the overtube 40, the distal end portion of the rigidity change region 2a is covered by the overtube 40.

FIGS. 6, 7, 8, and 9 show manners of change in rigidity of the insertion section 2 and the overtube 40 in the longitudinal direction. In schematic graphs shown in FIGS. 6, 7, 8, and 9, an x-axis, which is a horizontal axis, indicates a distance in the longitudinal direction from the distal end of the insertion section 2, and a y-axis, which is a vertical axis, indicates rigidity to deformation in a bending direction of the insertion section 2 and the overtube 40.

With respect to the x-axis, x=0 is the distal end of the insertion section 2, and x=L0 is the proximal end of the insertion section 2 (i.e., the proximal end 10b of the flexible tube portion 10). With respect to the y-axis, rigidity is increased toward an upper side in the drawing. A one-dot chain line in the drawing indicates the rigidity of the insertion section 2, and a two-dot chain line indicates the rigidity of the overtube 40. A value obtained by adding the rigidity of the insertion section 2 and the rigidity of the overtube 40 at an x-coordinate indicates the rigidity of the insertion section 2 of the endoscope system 50 at the x-coordinate.

Figure 6:
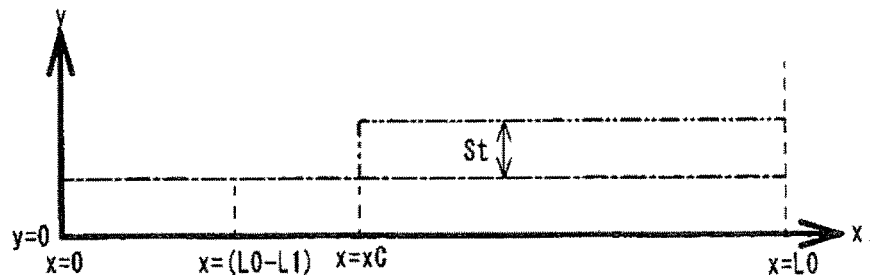
FIG. 6 is a diagram schematically showing a manner of change in rigidity of the insertion section of the endoscope system.

FIG. 6 shows a state where the distal end portion of the rigidity change region 2a is exposed from the overtube 40 in the distal end direction, and where an increase operation of the rigidity of the flexible tube portion 10 by the rigidity changing mechanism portion 20 is not performed. That is, in the state shown in FIG. 6, a value at an x-coordinate xC of the distal end of the overtube 40 is greater than L0−L1.

As shown in FIG. 6, in a region (x≥xC) covered by the overtube 40, rigidity St of the cylindrical portion 41 of the overtube 40 is combined with the rigidity of the insertion section 2, and thus, the rigidity is increased.

Note that, in FIG. 6, for the sake of description, the rigidity of the insertion section 2 of the endoscope is indicated to take a constant value 11 regardless of the x-coordinate, but the rigidity of the insertion section 2 may change according to a change in the x-coordinate. The same thing can be said for FIGS. 7, 8, and 9.

Figure 7:
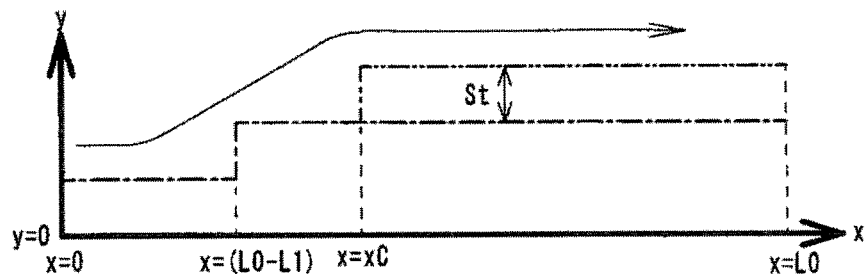
FIG. 7 is a diagram schematically showing a manner of change in rigidity of the insertion section of the endoscope system.

FIG. 7 shows a state where the distal end portion of the rigidity change region 2a is exposed from the overtube 40 in the distal end direction, and where the increase operation of the rigidity of the flexible tube portion 10 by the rigidity changing mechanism portion 20 is performed.

In the state shown in FIG. 7, the rigidity of the rigidity change region 2a of the insertion section 2 is increased. The rigidity change region 2a is a region where the x-coordinate is greater than L0-L1. In the state shown in FIG. 7, the distal end of the overtube 40 is positioned inside the rigidity change region 2a.

That is, a region where the rigidity is increased by being covered with the overtube 40 is positioned on the proximal end side with respect to the distal end of the rigidity change region 2a. Accordingly, in the state shown in FIG. 7, rigidity is lowest in a first region (x<(L0-L1)) which is on the distal end side with respect to the rigidity change region 2a, middle in a second region ((L0-L1)≤x<xC), of the rigidity change region 2a, which is exposed from the overtube 40 in the distal end direction, and highest in a third region (x≥xC), of the rigidity change region 2a, which is covered by the overtube 40.

The first region, the second region, and the third region where the rigidity is gradually increased in such an order are disposed in order from the distal end of the insertion section 2 toward the proximal end direction. Accordingly, in the state shown in FIG. 7, the rigidity is slowly increased from the distal end of the insertion section 2 toward the proximal end direction. When inclination of the change in the rigidity from the distal end of the insertion section 2 toward the proximal end direction is gradual, insertability at the time of insertion of the insertion section 2 into a subject is increased.

Figure 8:
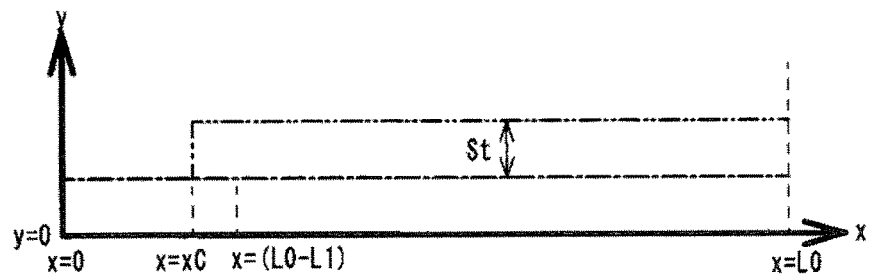
FIG. 8 is a diagram schematically showing a manner of change in rigidity of the insertion section of the endoscope system.

FIG. 8 shows a state where the distal end portion of the rigidity change region 2a is covered by the overtube 40, and where the increase operation of the rigidity of the flexible tube portion 10 by the rigidity changing mechanism portion 20 is not performed. That is, in the state shown in FIG. 8, the value at the x-coordinate xC of the distal end of the overtube 40 is smaller than L0-L1.

Figure 9:
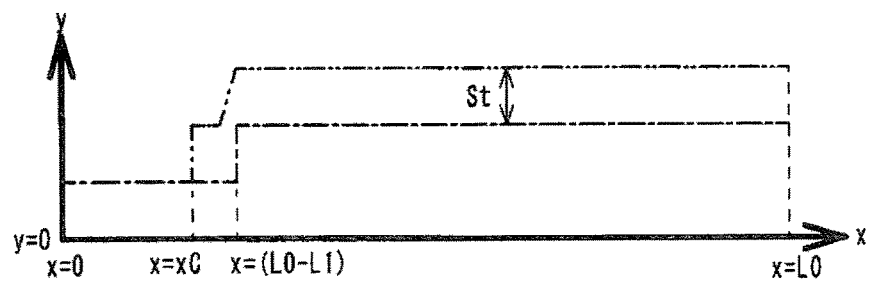
FIG. 9 is a diagram schematically showing a manner of change in rigidity of the insertion section of the endoscope system.

FIG. 9 shows a state where the distal end portion of the rigidity change region 2a is covered by the overtube 40, and where the increase operation of the rigidity of the flexible tube portion 10 by the rigidity changing mechanism portion 20 is performed.

In the present embodiment, an increase width St of the rigidity due to covering with the overtube 40 is set to be equal to an increase width of the rigidity of the flexible tube portion 10 achieved by the rigidity changing mechanism portion 20. Accordingly, in the present embodiment, when the distal end of the overtube 40 is positioned on the distal end side with respect to the rigidity change region 2a, the rigidity of the flexible tube portion 10 may be increased without performing the rigidity increase operation by the rigidity changing mechanism portion 20, as shown in FIG. 8.

Next, a method of inserting the insertion section 2 of the endoscope 1 into a large intestine 60 of a human body, which is a subject, through an anus 61 by using the endoscope system 50 of the present embodiment will be described with reference to FIGS. 10 to 17.

Figure 10:
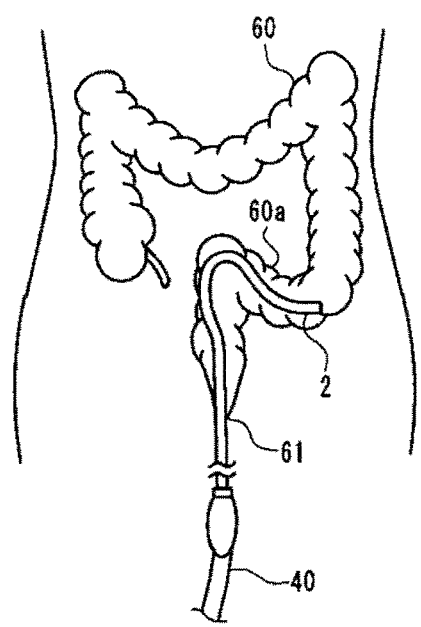
FIG. 10 is a diagram describing a first step of an insertion method using the endoscope system.

First, as shown in FIG. 10, in a first step, only the insertion section 2 of the endoscope 1 is inserted from the anus 61 until the distal end reaches a sigmoid colon 60a of the large intestine 60, in a state where the increase operation of the rigidity of the flexible tube portion 10 by the rigidity changing mechanism portion 20 is not performed. Here, the insertion section 2 is covered by the overtube 40 while being in a state where the overtube 40 is drawn toward the proximal end 10b side of the flexible tube portion 10 (i.e., the operation section 3 side). That is, the overtube 40 is positioned outside the anus 61.

In the first step, the range of the insertion section 2, which is inserted in the large intestine 60 is not covered by the overtube 40, and the increase operation of the rigidity of the flexible tube portion 10 by the rigidity changing mechanism portion 20 is not performed, and thus, the rigidity is the lowest and the insertion section 2 is soft. Accordingly, the insertion section 2 may be easily moved forward inside the sigmoid colon 60a with many flexions.

Figure 11:
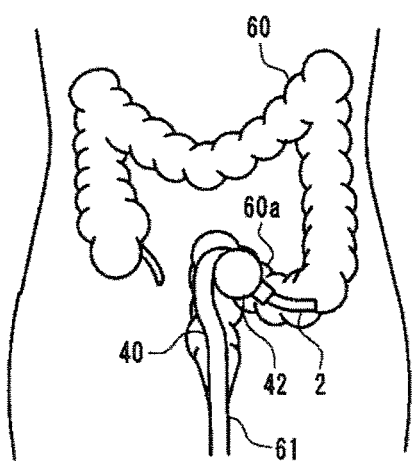
FIG. 11 is a diagram describing a second step of the insertion method using the endoscope system.

Next, as shown in FIG. 11, in a second step, the overtube 40 is moved in the distal end direction along the insertion section 2 so that the distal end of the overtube 40 reaches the sigmoid colon 60a. Here, the overtube 40 is positioned on the distal end side with respect to the distal end of the rigidity changing mechanism portion 20. Due to such an operation, the rigidity of the insertion section 2 covered by the overtube 40 is increased, as shown in FIG. 8.

Then, air is sent into the balloon 42 from the balloon air port 43 to expand the balloon 42, and a position of the overtube 40 is fixed.

Figure 12:
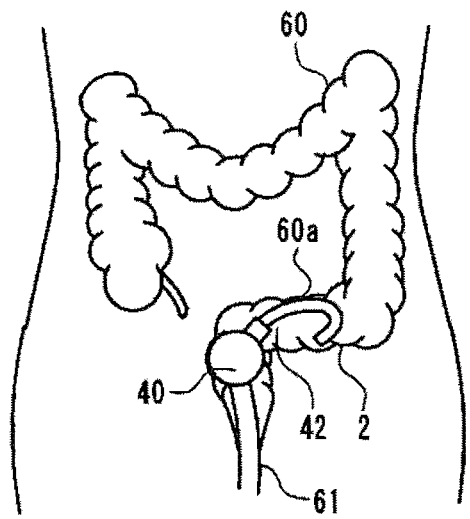
FIG. 12 is a diagram describing a third step of the insertion method using the endoscope system.

Next, as shown in FIG. 12, in a third step, the sigmoid colon 60a is straightened by pulling the overtube 40, the position of which is fixed, and the insertion section 2 with increased rigidity. Moreover, the increase operation of the rigidity of the flexible tube portion 10 by the rigidity changing mechanism portion 20 is performed.

Figure 13:
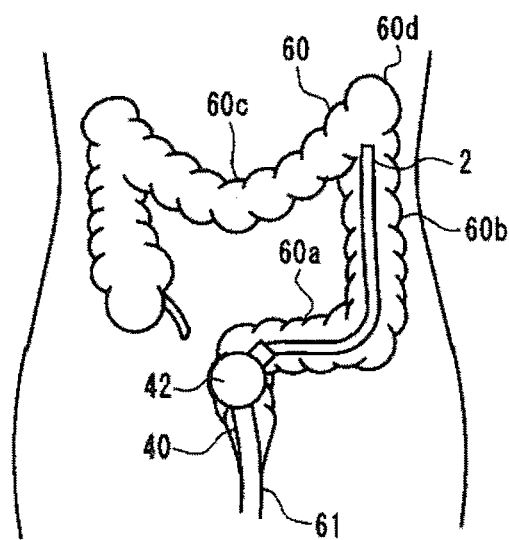
FIG. 13 is a diagram describing a fourth step of the insertion method using the endoscope system.

Next, as shown in FIG. 13, in a fourth step, the insertion section 2 on which the rigidity increase operation is performed is pushed in while the position of the overtube 40 is maintained fixed, and the distal end of the insertion section 2 is moved forward to a splenic flexure 60d between a descending colon 60b and a transverse colon 60c. Here, as shown in FIG. 7, the rigidity of the insertion section 2 is gradually increased from the distal end in the proximal end direction. That is, the distal end side of the insertion section 2 where the rigidity is low may be easily moved forward, while maintaining the rigidity of a part, of the insertion section 2, on the proximal end side which is inserted in the straightened sigmoid colon 60a.

Figure 14:
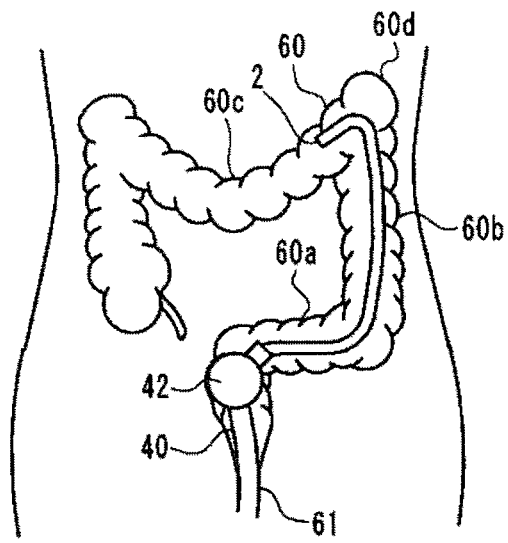
FIG. 14 is a diagram describing a fifth step of the insertion method using the endoscope system.

Then, as shown in FIG. 14, in a fifth step, the distal end of the insertion section 2 is moved forward into the transverse colon 60c.

Figure 15:
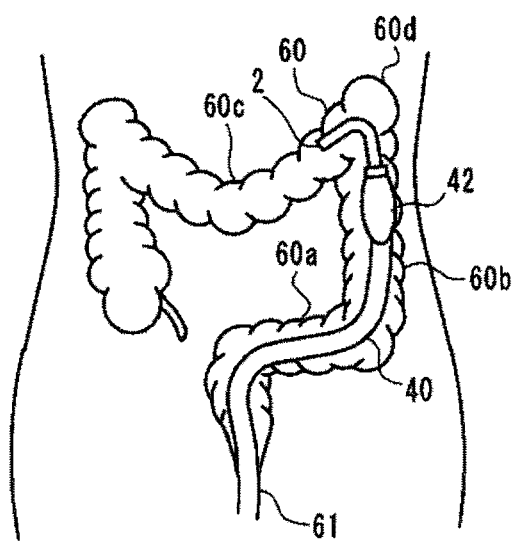
FIG. 15 is a diagram describing a sixth step of the insertion method using the endoscope system.

Next, as shown in FIG. 15, in a sixth step, after the balloon 42 is contracted, the overtube 40 is moved in the distal end direction along the insertion section 2, and the distal end of the overtube 40 is moved forward to the splenic flexure 60d. Then, a state is reached where the increase operation of the rigidity of the flexible tube portion 10 by the rigidity changing mechanism portion 20 is not performed.

At this time, as shown in FIG. 8, the rigidity of the flexible tube portion 10 is increased due to the presence of the overtube 40, even if the rigidity increase operation by the rigidity changing mechanism portion 20 is not performed. Accordingly, the shape of the straightened sigmoid colon 60a is maintained.

Figure 16:
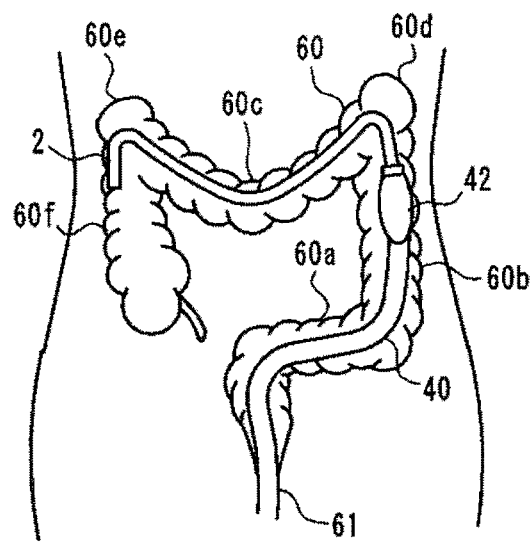
FIG. 16 is a diagram describing a seventh step of the insertion method using the endoscope system.

Next, as shown in FIG. 16, in a seventh step, in a state where the increase operation of the rigidity of the flexible tube portion 10 by the rigidity changing mechanism portion 20 is not performed, the position of the overtube 40 is fixed, and only the insertion section 2 is moved forward until the distal end reaches a hepatic flexure 60e. Here, the shape of the sigmoid colon 60a which is straightened due to the rigidity of the overtube 40 is maintained, and also, a range, of the insertion section 2, which is inserted in the large intestine 60 is soft and the rigidity is the lowest because the increase operation of the rigidity of the flexible tube portion 10 by the rigidity changing mechanism portion 20 is not performed and the range is not covered by the overtube 40, and thus, the insertion section 2 may be easily moved forward in the transverse colon 60c with many flexions and which is not fixed (in a rigid state, insertion is difficult because a flexed portion of the transverse colon greatly hangs down toward the anus).

Figure 17:
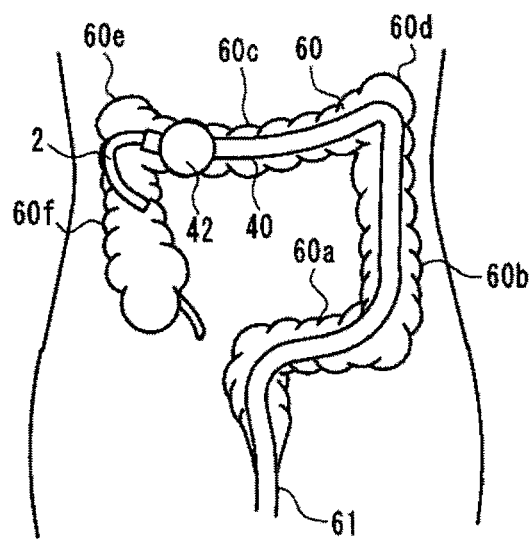
FIG. 17 is a diagram describing an eighth step of the insertion method using the endoscope system.

Next, as shown in FIG. 17, in an eighth step, the increase operation of the rigidity of the flexible tube portion 10 by the rigidity changing mechanism portion 20 is performed, and the transverse colon 60c is lifted up. Then, the overtube 40 is moved in the distal end direction along the insertion section 2, and the distal end of the overtube 40 is moved forward to the hepatic flexure 60e, and the balloon 42 is expanded to fix the position of the overtube 40.

When the distal end of the overtube 40 is fixed near the hepatic flexure 60e, shapes of the straightened sigmoid colon 60a and the lifted transverse colon 60c are maintained, and thus, an operation of moving the insertion section 2 forward to an ascending colon 60f, which is located even deeper in the large intestine, is facilitated.

As described above, the endoscope system 50 of the present embodiment enables an insertion operation of the insertion section 2 into a subject to be easily performed, by allowing setting of various levels of rigidity (i.e., by increasing the degree of freedom regarding setting of rigidity in the longitudinal direction) by combining switching between performance and non-performance of the increase operation of rigidity of the flexible tube portion 10 by the rigidity changing mechanism portion 20, and forward/backward movement of the overtube 40 in the longitudinal direction relative to the insertion section 2.

The present invention is not limited to the embodiment described above, and changes may be made as appropriate without departing from the essence or idea of the invention that can be read from the claims and the entire specification. An endoscope system involving such changes is also included within the technical scope of the present invention.

What is claimed is:

1. An endoscope system comprising:
    an endoscope including
        an insertion section formed in an elongated shape,
        a flexible tube portion provided at a proximal end side of the insertion section, and
        a rigidity changing mechanism portion provided inside the flexible tube portion, and configured to change rigidity of the flexible tube portion, where a rigidity change region of the flexible tube portion by the rigidity changing mechanism portion is set to be from an intermediate portion to a proximal end portion of the flexible tube portion; and
    a flexible overtube formed in a cylindrical shape extending in an axial direction, into which the insertion section is slidably inserted, where the overtube is formed to have a total length in the axial direction that is shorter than a total length of the rigidity change region, and a degree of increase in rigidity in a state of covering the insertion section is set to be substantially equal to a degree of increase in the rigidity of the flexible tube portion caused by operation of the rigidity changing mechanism portion, wherein
    by allowing, by changing relative positions of the overtube and the insertion section in a longitudinal direction in a state where the insertion section is covered by the overtube, selection between a state where a proximal end portion of the overtube in the axial direction is positioned on a most proximal end side of the insertion section and a distal end portion of the rigidity change region is exposed and a state where the overtube is displaced to a distal end side and the distal end portion of the rigidity change region is covered by the overtube, and by setting a degree of increase in rigidity, at a part of the insertion section where the overtube is covered, caused by the overtube covering the insertion section, to be substantially equal, in a state where the insertion section is covered by overtube, to the degree of increase in the rigidity of the flexible tube portion caused by operation of the rigidity changing mechanism portion, rigidity of a part of the insertion section which is on a distal end side with respect to the rigidity change region, a part of the rigidity change region exposed from the overtube, and a part covered by the overtube is gradually increased stepwise from a distal end of the insertion section in a proximal end direction, when an increase operation of rigidity of the rigidity change region is performed by the rigidity changing mechanism portion while the state where the proximal end portion of the overtube in the axial direction is positioned on the most proximal end side of the insertion section and the distal end portion of the rigidity change region is exposed is selected.

2. The endoscope system according to claim 1, wherein an expandable balloon is disposed on an outer circumference of a distal end of the overtube.

* * * * *